US011478455B2

(12) United States Patent
Immig et al.

(10) Patent No.: US 11,478,455 B2
(45) Date of Patent: *Oct. 25, 2022

(54) USE OF BIOTIN AND NATURAL ESSENTIAL OILS FOR BOVINE ANIMALS FOR THE PREVENTION AND TREATMENT OF KETOSIS

(71) Applicant: DSM IP ASSETS B.V., Heerlen (NL)

(72) Inventors: Irmgard Immig, Kaiseraugst (CH); Wolfgang Steinberg, Kaiseraugst (CH); Joseph McGrath, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/131,739

(22) Filed: Dec. 22, 2020

(65) Prior Publication Data
US 2021/0106565 A1 Apr. 15, 2021

Related U.S. Application Data

(63) Continuation of application No. 15/102,316, filed as application No. PCT/EP2014/077399 on Dec. 11, 2014, now Pat. No. 10,952,991.

(30) Foreign Application Priority Data

Dec. 13, 2013 (EP) .................................... 13197170
Feb. 24, 2014 (EP) .................................... 14156282

(51) Int. Cl.
| | | |
|---|---|---|
| *A61K 31/4188* | (2006.01) | |
| *A61K 31/05* | (2006.01) | |
| *A61K 31/11* | (2006.01) | |
| *A23K 20/174* | (2016.01) | |
| *A23K 20/158* | (2016.01) | |
| *A23K 50/10* | (2016.01) | |
| *A23K 20/10* | (2016.01) | |
| *A61K 31/085* | (2006.01) | |

(52) U.S. Cl.
CPC .......... *A61K 31/4188* (2013.01); *A23K 20/10* (2016.05); *A23K 20/158* (2016.05); *A23K 20/174* (2016.05); *A23K 50/10* (2016.05); *A61K 31/05* (2013.01); *A61K 31/085* (2013.01); *A61K 31/11* (2013.01)

(58) Field of Classification Search
CPC .... A61K 2300/00; A61K 31/05; A61K 31/11; A61K 31/4188; A61K 31/085; A23K 20/10; A23K 20/158; A23K 20/174; A23K 50/10; A61P 3/00; A61P 43/00
See application file for complete search history.

(56) References Cited

U.S. PATENT DOCUMENTS

| | | |
|---|---|---|
| 5,565,211 A | 10/1996 | Rossi |
| 2003/0211136 A1 | 11/2003 | Kulkarni et al. |
| 2009/0004308 A1 | 1/2009 | Frehner |
| 2010/0310740 A1 | 12/2010 | Kim et al. |

FOREIGN PATENT DOCUMENTS

| | | |
|---|---|---|
| CN | 1088745 | 7/1994 |
| CN | 101331915 | 12/2008 |
| CN | 102302163 | 1/2012 |
| CN | 102885236 | 1/2013 |
| CN | 103330087 | 10/2013 |
| CN | 102239962 | 7/2014 |
| SU | 680714 | 8/1978 |
| WO | 99/59430 | 11/1999 |
| WO | 01/91577 | 12/2001 |

OTHER PUBLICATIONS

Potter, JSTOR, Journal of Zoo and Wildlife Medicine, vol. 36, No. 2 (Jun. 2005), pp. 301-307). (Year: 2005).*
Ketosis in Cattle, MERCK (Year: 2021).*
International Search Report for PCT/EP2014/077399, dated Feb. 2, 2015, 1 page.
Gordon, "Risk Factors for and Treatment of Ketosis in Lactating Dairy Cattle", A Thesis Presented to the University of Guelph, Aug. 1, 2013, 174 pages.
Janis Hausmann et al., PLoS ONE 13(3): e0193685. https://doi.org/10.1371/journal.pone.0193685 (Mar. 27, 2018).
Janis Hausmann et al., Animal Feed Science and Technology, 225(2017): 23-27.
O. Rosendo et al., "Effects of Biotin Supplementation on Peripartum Performance and Metabolites of Holstein Cows," J. Dairy Sci. 87:2535-2545, American Dairy Science Association, 2004.
Wall, Countryside & Small Stock Journal, Jul./Aug. 2010 (Year: 2010).
Buchoo et al, Indian Vet J, Jun. 2007, 84, 659. (Year: 2007).
Biomin, 2020, https://www.biomin.net/species/ruminants/ketosis/ (Year: 2020).
Ballarat, Note No. AG0210, Jul. 2007, (Year: 2007).
Rosendo et al., J. Diary Sci. 87, 2535-2545, 2004 (Year: 2004).

(Continued)

*Primary Examiner* — Umamaheswari Ramachandran
(74) *Attorney, Agent, or Firm* — Nixon & Vanderhye P.C.

(57) ABSTRACT

Methods to prevent ketosis or minimize the effects of ketosis in ruminant animals are provided. This methods include feeding to the animal biotin in combination with a mixture of at least two essential oil compounds selected from the group consisting of thymol, eugenol, meta-cresol, vaniline and guajacol. The methods usefully prevent and/or inhibit ketosis of calving ruminant animals and the subsequent need for veterinary treatment. In a preferred embodiment of a feeding concept for dairy cattle, especially calving dairy cattle, biotin is used in an amount sufficient to provide a daily dosage of 10 mg to 20 mg per head to which it is to be administered. It is at present contemplated that the essential oils are administered in amounts (total dosage ranges of essential oils) of 1 to 1.5 g per head per day.

6 Claims, No Drawings

(56) References Cited

OTHER PUBLICATIONS

Cavini S. et al., "An encapsulated blend of cinnamaldehyde, eugenol and capsicum oleoresin limits the risk of metabolic diseases in transition dairy ruminants", Freising, pp. 157-160, XP05543847 (2012).

Cavini S. et al., "Essential Oils May Reduce the Risk of Ketosis in Dairy Goats Carrying Twins", XIII Jorandoas sobre Produccion Animal, AIDA (2009) (Abstract).

Janis Hausmann et al; "Effects of combined supplementation with plant bioactive lipid compounds and biotin on ruminal fermentation, body condition and energy metabolism in transition dairy cows", Animal Feed Science and Technology 225 (2017) 27-37.

Janis Hausmann et al, "Effects of a combination of plant bioactive lipid compounds and biotin compared with monensin on body condition, energy metabolism and milk performance in transition dairy cows", PLOS One, https://doi.org/10.1371/journal.pone.0193685 (Mar. 27, 2018).

Chen et al, "Effect of biotin on milk performance of dairy cattle: A meta-analysis," J. Dairy Sci. 94:3537-3546, American Dairy Science Association®, China, 2011.

Duffield, "Ketosis in Cattle," Merck Manual Veterinary Manual, Merck Sharp & Dohme Corp, a Subsidiary of Merck & Co., Inc., NJ, 2021, pp. 1-3.

Enjalbert et al, "Effects of peripartum biotin supplementation of dairy cows on milk production and milk composition with emphasis on fatty acids profile," Livestock Science 114 (2008) 287-295.

Fox, "Clinical Diagnosis and Treatment of Ketosis," Ambulatory Clinic, Cornell University, NY, Journal of Dairy Science vol. 54, No. 6, 1971, pp. 974-978.

Lean et al, "Effect of feeding biotin on milk production and hoof health in lactating dairy cows: A quantitative assessment," Journal of Dairy Science vol. 94 No. 3, 2011, pp. 1465-1477.

Potter et al, "Mortality of Captive Giraffe (*Giraffa camelopardalis*) Associated With Serous Fat Atrophy: A Review of Five Cases at Auckland Zoo", Journal of Zoo and Wildlife Medicine 36(2): 301-307, 2005.

\* cited by examiner

USE OF BIOTIN AND NATURAL ESSENTIAL OILS FOR BOVINE ANIMALS FOR THE PREVENTION AND TREATMENT OF KETOSIS

CROSS-REFERENCE SECTION

This application is a continuation of commonly owned U.S. application Ser. No. 15/102,316 (now U.S. Pat. No. 10,952,991), filed Jun. 7, 2016 which is the U.S. national phase of International Application No. PCT/EP2014/077399 filed Dec. 11, 2014 which designated the U.S. and claims priority to EP Patent Application Nos. 13197170.7 filed Dec. 13, 2013 and 14156282.7 filed Feb. 24, 2014, the entire contents of each of which are hereby incorporated by reference.

BACKGROUND OF THE INVENTION

The present invention is directed to the field of nutritional supplements for ruminant animals, especially dairy cattle, before, during and after calving. More particularly, the present invention is directed to a nutritional supplement in a unit dosage form that is capable of preventing or minimizing the effects of ketosis that commonly afflict calving ruminant animals, especially calving dairy cattle.

The present invention is useful because it is capable of preventing and/or inhibiting ketosis of calving ruminant animals and the subsequent need for veterinary treatment.

Therefore, this invention relates to a method of prevention of ketosis or minimizing the effects of ketosis in cattle.

Ketosis is an acute disease often attacking cattle which obstructs the metabolism of carbohydrates and fats in the organism of cattle. As the result, a ketone body such as acetoacetate, beta-hydroxybutyrate and acetone increases in the cattle blood, giving rise to the odor of acetone in the urine, milk and breath of cattle.

A cow affected by the ketosis presents major clinical symptoms such as anorexia or loss of appetite, rapid decrease of weight and a sharp drop in the yield of milk.

Ketosis may or may not occur with hypocalcemia. At the start of lactation, there is a sudden and heavy demand for the production of lactose for the milk. This causes a depletion of the animal's blood sugar (glucose). If the animal does not have a sufficient reserve of carbohydrate in the liver and/or a sufficient source in the feed, then it must rely on an alternative source of energy, its own body fat.

When fat is metabolized, the result is not glucose but ketone. While ketones can provide energy to muscle, they cannot supply energy needed as glucose, to the brain. As a result, the animal may become anorexic or exhibit bizarre behavior. The condition is also known as hypoglycemia.

SUMMARY OF THE INVENTION

The present inventors now surprisingly found that compositions containing biotin in combination with a mixture of at least two essential oil compounds selected from the group consisting of thymol, eugenol, meta-cresol, vaniline and guajacol can be used for the prevention and treatment of ketosis.

Therefore, the present invention relates to the use of biotin in combination with a mixture of at least two essential oil compounds selected from the group consisting of thymol, eugenol, meta-cresol, vaniline and guajacol in feed for animals of the subfamily Bovinae for the prevention of ketosis or minimizing the effects of ketosis in cattle.

In the present context, an animal of the subfamily Bovinae (also called bovines or bovine animals) means an animal of the kingdom of Animalia, the phylum of Chordata, the class of Mammalia, the order of Artiodactyla, and the family of Bovidae. For the present purposes, Domestic cattle are the most preferred species. For the present purposes the term includes all races of domestic cattle, and all production kinds of cattle, in particular dairy cows.

More particularly, this invention relates to the use of a composition as defined above as a component of animal feed or drinking water or feed or drinking water additives, as well as to compositions, feed additives, drinking water and feed containing them.

The term feed or feed composition means any compound, preparation, mixture, or composition suitable for, or intended for intake by an animal.

Biotin can occur in eight different stereoisomeric forms and is a known active ingredient, which can be found in numerous pharmaceutical compositions. Biotin is commercially available (for example as Rovimix® Biotin, supplied by DSM Nutritional Products, Kaiseraugst, Switzerland) or can be prepared by a skilled person using processes and methods well-known in the prior art.

The essential oil compounds according to the invention are commercially available or can be prepared by a skilled person using processes and methods well-known in the prior art.

The essential oil compounds can be used in highly purified forms in mixtures or in the form of natural available plant extracts or extract-mixtures.

The term "extract" as used herein includes compositions obtained by solvent extraction (which are also known as "extracted oils"), steam distillation (which are also known as "essential oils") or other methods known to the skilled person. Suitable extraction solvents include alcohols such as ethanol.

By the expression "natural" is in this context understood a substance which consists of compounds occurring in nature and obtained from natural products or through synthesis. The natural substance may preferably contain at least two of the compounds as defined above as main ingredient and additionally other essential oil compounds as for example capsaicin, tannin or carvacrol.

The present invention also relates to the method for the prevention of ketosis or minimizing the effects of ketosis in cattle, which comprises providing to a dairy cattle an effective amount of biotin in combination with a mixture of at least two essential oil compounds selected from the group consisting of thymol, eugenol, meta-cresol, vaniline and guajacol during a period of up to 4 to 6 weeks before calving and/or up to a period of 50 to 100 days after calving.

In a preferred embodiment of a feeding concept for dairy cattle, especially calving dairy cattle, biotin being used in an amount sufficient to provide a daily dosage of 10 mg to 20 mg per head to which it is to be administered.

It is at present contemplated that the essential oils are administered in amounts (total dosage ranges of essential oils) of 1 to 1.5 g per kg head per day.

In another preferred embodiment of the invention the essential oils are added to the feed as a single feed additive composition.

The feed additive composition containing the essential oils according to the invention may optionally contain in minor amounts other chemical compounds, for example at least one compound found in plants, and selected from the following group, as, per kg of feed:

up to about 1 mg of propylidene, butylidene, phtalides, gingerol, lavender oil;

up to about 2 mg of deca-, undeca-, dodecalactones, ionones, irone, eucalyptol, menthol, peppermint oil, alpha-pinene;

up to about 3 mg of limonene, anethol, linalool, methyl dihydrojasmonate;

up to about 4 mg of carvacrol, propionic, acetic or butyric acid, rosemary oil, clove oil, geraniol, terpineol, citronellol;

up to about 5 mg of amyl and/or benzyl salicylate, cinnamaldehyde, a plant polyphenol (tannin);

and up to about 5 mg of a powder of turmeric or of an extract of curcuma.

All the essential oils and the additional compounds may be used in combination with an emulsifying surfactant.

The emulsifying agent can be selected advantageously from those of a rather hydrophilic nature, for example among polyglycerol esters of fatty acids such as esterified ricinoleic acid or propylene glycol esters of fatty acids, saccharo-esters or saccharo-glycerides, polyethylene glycol, lecithins etc.

Examples of particularly preferred dosages of the essential oil compounds in a final feed additive composition according to the invention are independently from each other in the following ranges:

thymol between 80 and 120 g/kg, preferably 101 g/kg;
eugenol between 20 and 60 g/kg, preferably 30 g/kg;
meta-cresol 80 and 110 g/kg, preferably 90 g/kg;
vaniline between 30 and 70 g/kg, preferably 50 g/kg
guajacol between 20 and 50 g/kg, preferably 35 g/kg
salicylate between 10 and 30 g/kg, preferably 25 g/kg
resorcine between 5 and 20 g/kg, preferably 15 g/kg In a preferred embodiment of a feeding concept the final feed includes biotin and a mixture of thymol, meta-cresol and vaniline, wherein these four compounds being used in amounts sufficient to provide a daily dosage of 10 mg to about 20 mg biotin and 1 g to 1.5 g total essential oils per head to which it is to be administered.

The term "feed" as used herein includes biotin and a feed additive composition according to the invention and other components. A typical cattle feed comprises as other components 60% to 90% corn or corn silage, between 3% and 10% SBM (Soya bean meal), 1% to 2% minerals and optionally between 5% and 20% hay, cereals and straw.

As regards feed compositions for bovines such as cows, as well as ingredients thereof, the bovine diet is usually composed of an easily degradable fraction (named concentrate) and a fibre-rich less readily degradable fraction (named hay, forage, or roughage).

Hay is made of dried grass, legume or whole cereals. Grasses include among others timothy, ryegrasses, and fescues. Legumes include among others clover, lucerne or alfalfa, peas, beans and vetches. Whole cereals include among others barley, maize (corn), oat, sorghum. Other forage crops include sugarcane, kales, rapes, and cabbages. Also root crops such as turnips, swedes, mangels, fodder beet, and sugar beet (including sugar beet pulp and beet molasses) are used to feed ruminants. Still further crops are tubers such as potatoes, cassava and sweet potato. Silage is an ensiled version of the fibre-rich fraction (e.g. from grasses, legumes or whole cereals) whereby material with a high water content is treated with a controlled anaerobic fermentation process (naturally-fermented or additive treated).

Concentrate is largely made up of cereals (such as barley including brewers grain and distillers grain, maize, wheat, sorghum), but also often contain protein-rich feed ingredients such as soybean, rapeseed, palm kernel, cotton seed and sunflower.

Cows may also be fed total mixed rations (TMR), where all the dietary components, e.g. forage, silage and concentrate, are mixed before serving.

The feed additive composition of the invention comprises, in addition to the ingredients according to the invention as described hereinabove, at least one additional ingredient selected from amongst vitamins and minerals. For example, the feed additive of the invention may include (i) at least one vitamin, (ii) at least one mineral, or (iii) at least one vitamin and at least one mineral.

The at least one vitamin may be fat-soluble or water-soluble. Examples of fat-soluble vitamins are vitamin A, vitamin D3, vitamin E, and vitamin K, e.g. vitamin K3. Examples of water-soluble vitamins are vitamin B12, biotin and choline, vitamin B1, vitamin B2, vitamin B6, niacin, folic acid and panthothenate, e.g. Ca-D-panthothenate.

The at least one mineral may be a macro minerals and/or a trace mineral. Examples of trace minerals are manganese, zinc, iron, copper, iodine, selenium, and cobalt. Examples of macro minerals are calcium, phosphorus and sodium.

Premixes are recognized terms in the art for certain feed additives. They may be solid or liquid. A mineral premix is a composition which is intended for addition to animal feed and which comprises desired kinds and amounts of minerals, in particular trace minerals. A vitamin premix is a composition which is intended for addition to animal feed and which comprises desired kinds and amounts of vitamins. Some premixes include both vitamins and minerals.

The invention claimed is:

1. A method for treating and/or minimizing effects of ketosis in domestic dairy cattle, wherein the method comprises administering to domestic dairy cattle during a period of up to 4 to 6 weeks before calving and/or up to a period of 50 to 100 days after calving an effective amount of biotin in combination with a mixture of at least two essential oil compounds selected from the group consisting of thymol, eugenol, meta-cresol, vaniline and guajacol to treat and/or minimize the effects of ketosis in the domestic dairy cattle.

2. The method according to claim 1, wherein biotin is administered in an amount sufficient to provide a daily dosage of 10 mg to 20 mg per head and wherein the mixture of the at least two essential oil compounds is administered in an amount sufficient to provide a total dosage range of the at least two essential oil compounds of 1 g to 1.5 g per head per day.

3. The method according to claim 1, wherein the method comprises the step of administering to the domestic dairy cattle a feed which includes a feed additive composition comprised of biotin and at least two of the following essential oil compounds selected from the group consisting of:

thymol in an amount between 80 and 120 g/kg feed;
eugenol in an amount between 20 and 60 g/kg feed;
meta-cresol in an amount between 80 and 110 g/kg feed;
vaniline in an amount between 30 and 70 g/kg feed;
guajacol in an amount between 20 and 50 g/kg feed;
salicylate in an amount between 10 and 30 g/kg feed; and
resorcine in an amount between 5 and 20 g/kg.

4. The method according to claim 1, wherein the method comprises the step of administering to the domestic dairy cattle a feed which includes a feed additive composition comprised of biotin and at least two of the following essential oil compounds selected from the group consisting of:
thymol in an amount of 101 g/kg feed;
eugenol in an amount of 30 g/kg feed;
meta-cresol in an amount of 90 g/kg feed;
vaniline in an amount of 50 g/kg feed;
guajacol in an amount of 35 g/kg feed;
salicylate in an amount of 25 g/kg feed; and
resorcine in an amount of 15 g/kg.

5. The method according to claim 1, wherein the mixture of essential oils comprises thymol, meta-cresol and vaniline.

6. The method according to claim 5, wherein
the thymol is present in an amount between 80 and 120 g/kg feed;
the meta-cresol is present in an amount between 80 and 110 g/kg feed; and
the vaniline is present in an amount between 30 and 70 g/kg feed.

\* \* \* \* \*